US011369752B2

(12) United States Patent
Wilsey et al.

(10) Patent No.: US 11,369,752 B2
(45) Date of Patent: Jun. 28, 2022

(54) DELIVERY OF THERAPEUTIC MATERIAL VIA SUB-LIGAMENTOUS SPACE

(71) Applicant: Warsaw Orthopedic, Inc., Warsaw, IN (US)

(72) Inventors: Jared T. Wilsey, Memphis, TN (US); Keith E. Miller, Germantown, TN (US); Benjamin T. Reves, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 572 days.

(21) Appl. No.: 16/391,242

(22) Filed: Apr. 22, 2019

(65) Prior Publication Data

US 2020/0330702 A1    Oct. 22, 2020

(51) Int. Cl.
*A61M 5/32* (2006.01)
*A61M 25/00* (2006.01)
*A61M 25/06* (2006.01)

(52) U.S. Cl.
CPC ........ *A61M 5/3297* (2013.01); *A61M 5/3287* (2013.01); *A61M 25/065* (2013.01); *A61M 2005/3201* (2013.01); *A61M 2025/0004* (2013.01); *A61M 2205/0266* (2013.01); *A61M 2210/1003* (2013.01)

(58) Field of Classification Search
CPC .............. A61M 5/3297; A61M 5/3287; A61M 25/065; A61M 2005/3201; A61M 2025/0004; A61M 2205/0266; A61M 2210/1003; A61B 2017/00261; A61B 17/1671; A61B 17/1757; A61B 2018/0044
See application file for complete search history.

(56) References Cited

U.S. PATENT DOCUMENTS

| 4,609,370 A * | 9/1986 | Morrison ........... A61B 17/3401 600/567 |
| 5,284,479 A | 2/1994 | de Jong |
| 6,517,568 B1 | 2/2003 | Sharkey |

(Continued)

FOREIGN PATENT DOCUMENTS

KR    20110118944 A    11/2011

OTHER PUBLICATIONS

International Search Report, PCT/US2019/057120, dated Feb. 6, 2020.

*Primary Examiner* — James D Ponton
(74) *Attorney, Agent, or Firm* — Fox Rothschild LLP; Paul Marshall Ticer

(57) ABSTRACT

An approach is provided for delivering therapeutic materials to an intervertebral disc via a sub-ligamentous space. The approach includes positioning a tool at an interface of a longitudinal ligament and an outer surface of the intervertebral disc, in which the interface is the sub-ligamentous space. The tool may include a first needle and a second needle housed within the first needle. An insertion end of the first needle may include a shallow beveled end. The approach includes inserting the insertion end of the first needle into the sub-ligamentous space. The approach includes deploying the second needle from within the first needle into at least one of an annulus and a nucleus of the intervertebral disc. The approach includes delivering the therapeutic materials to the at least one of the annulus and the nucleus.

20 Claims, 9 Drawing Sheets

(56) References Cited

U.S. PATENT DOCUMENTS

| | | |
|---|---|---|
| 7,824,390 B2 | 11/2010 | Miller et al. |
| 8,052,661 B2 | 11/2011 | McGuckin, Jr. et al. |
| 8,082,043 B2 | 12/2011 | Sharkey et al. |
| 8,540,684 B2 | 9/2013 | Yeung et al. |
| 9,113,950 B2 | 8/2015 | Schultz et al. |
| 2002/0016583 A1* | 2/2002 | Cragg .................. A61F 2/4465 604/500 |
| 2006/0206116 A1 | 9/2006 | Yeung |
| 2011/0276001 A1* | 11/2011 | Schultz .............. A61B 17/3478 604/164.01 |
| 2018/0207004 A1* | 7/2018 | Yeung ...................... A61F 2/44 |
| 2018/0256364 A1 | 9/2018 | Sandhu |
| 2019/0008528 A1 | 1/2019 | Lopez |
| 2019/0029844 A1 | 1/2019 | Schaller et al. |

\* cited by examiner

DELIVERY OF THERAPEUTIC MATERIAL VIA SUB-LIGAMENTOUS SPACE

BACKGROUND

As a human ages, the human's spine may show increasing signs of degeneration. Typically, early stages of spine degeneration may be treated with conservative care, whereas late stages of spine degeneration may include structural changes to the spine that necessitate fusion surgery. However, patients in the intermediate stages of spine degeneration often suffer from painful disc degeneration that is not responsive to conservative care, leaving patients with few options to address their discogenic pain.

In recent years, several regenerative therapies and treatments have been developed to aid in the biologic and chemical recovery of intervertebral disc degeneration. In these therapies and treatments, therapeutic materials may be delivered to an intervertebral disc, in order to address the discogenic pain and/or degenerative changes in the annulus fibrosus and, in particular, the nucleus pulpous of the intervertebral disc.

Delivering therapeutic material to the intervertebral disc requires breaching the intervertebral disc in at least one of the outer annulus fibrosus or the endplate of a vertebra, via a needle. However, the needle that delivers the therapeutic material creates a pathway in the intervertebral disc for the therapeutic material to exit the intervertebral disc. Given the significant spikes in intradiscal pressure during a patient's daily activities, the therapeutic material may be expelled at least in part from the intervertebral disc via the pathway created by the needle. Additionally, transosseous delivery of the therapeutic materials via an endplate of a vertebral body may avoid damage to the outer annulus fibrosus; however, this delivery approach may impact the endplate, which provides the primary source of oxygen and nutrients to the nearly avascular intervertebral disc.

SUMMARY

The present disclosure relates generally to devices and methods for treating damaged and/or diseased discs. In particular, the present disclosure relates to devices and methods for delivering regenerative medicine and/or therapeutic materials (hereinafter "therapeutic materials") to an intervertebral disc via sub-ligamentous space.

In one or more embodiments, the disclosed technology relates to a method of delivering therapeutic materials to an intervertebral disc via a sub-ligamentous space. In one or more embodiments, the method includes positioning a tool at an interface of a longitudinal ligament and an outer surface of the intervertebral disc, in which the interface is the sub-ligamentous space. In one or more embodiments, the tool includes a first needle and a second needle housed within the first needle, and an insertion end of the first needle includes a shallow beveled end. In one or more embodiments, the method includes inserting the insertion end of the first needle into the sub-ligamentous space. In one or more embodiments, the method includes deploying the second needle from within the first needle into at least one of an annulus and a nucleus of the intervertebral disc. In one or more embodiments, the method includes delivering the therapeutic materials to the at least one of the annulus and the nucleus.

In one or more embodiments, the disclosed technology relates to a posterolateral transforaminal method of delivering therapeutic materials to an intervertebral disc. In one or more embodiments, the method includes positioning a tool at an interface of a posterior longitudinal ligament and an outer surface of the intervertebral disc, in which the interface is the sub-ligamentous space. In one or more embodiments, the tool includes a first needle and a second needle housed within the first needle, and an insertion end of the first needle includes a shallow beveled end. In one or more embodiments, the method includes inserting the insertion end of the first needle into the sub-ligamentous space. In one or more embodiments, the method includes deploying the second needle from within the first needle into at least one of an annulus and a nucleus of the intervertebral disc, via a posterior portion or a posterolateral portion of the intervertebral disc. In one or more embodiments, the method includes delivering the therapeutic materials to the at least one of the annulus and the nucleus.

In one or more embodiments, the disclosed technology relates to a method of delivering therapeutic materials to an intervertebral disc. In one or more embodiments, the method includes positioning a tool at an interface of an anterior longitudinal ligament and an outer surface of the intervertebral disc, in which the interface is the sub-ligamentous space. In one or more embodiments, the tool includes a first needle and a second needle housed within the first needle, and an insertion end of the first needle includes a shallow beveled end. In one or more embodiments, the method includes inserting the insertion end of the first needle into the sub-ligamentous space. In one or more embodiments, the method includes deploying the second needle from within the first needle into at least one of an annulus and a nucleus of the intervertebral disc, via an anterior portion or an anterolateral portion of the intervertebral disc. In one or more embodiments, the method includes delivering the therapeutic materials to the at least one of the annulus and the nucleus.

The foregoing and other objects, features and advantages of the invention will be apparent from the following more particular descriptions of exemplary embodiments of the invention as illustrated in the accompanying drawings wherein like reference numbers generally represent like parts of the disclosure.

BRIEF DESCRIPTION OF DRAWINGS

The following drawings are illustrative of particular embodiments of the present disclosure and therefore do not limit the scope of the present disclosure. The drawings are not to scale and are intended for use in conjunction with the explanations in the following detailed description.

DETAILED DESCRIPTION

Figure 1A:
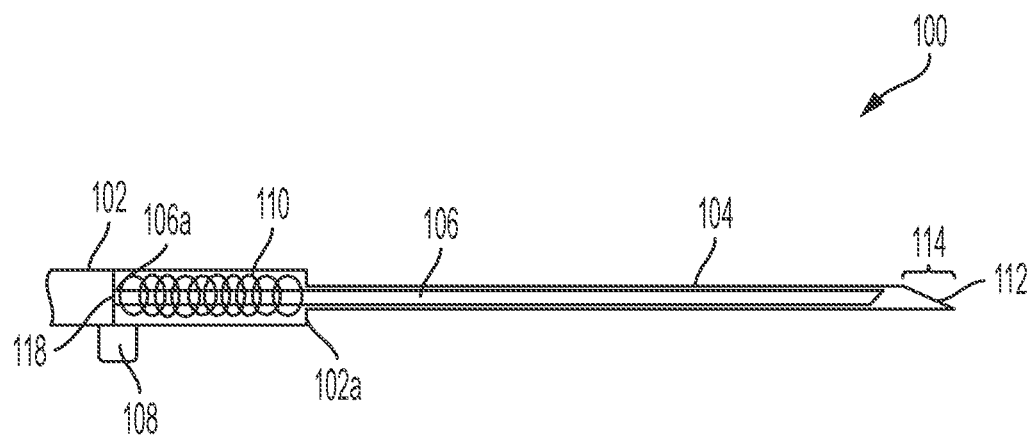
FIG. 1A illustrates a cross-sectional side view of an embodiment of a tool in a default position.

The following discussion omits or only briefly describes certain conventional features related to treating damaged and/or diseased discs which are apparent to those skilled in the art. It is noted that various embodiments are described in detail with reference to the drawings, in which like reference numerals represent like parts and assemblies throughout the several views. Reference to various embodiments does not limit the scope of the claims appended hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Embodiments of the present disclosure relate generally, for example, to devices and methods for treating damaged and/or diseased discs. In particular, embodiments of the present disclosure relate to devices and methods for delivering regenerative medicine and/or therapeutic materials (hereinafter "therapeutic materials") to an intervertebral disc via sub-ligamentous space. In one or more embodiments, therapeutic materials may include cells, such as stem cells, discogenic cells, platelet rich plasma, blood, bone marrow concentrate, and other cell-containing compositions; proteins, such as cytokines, growth and differentiation factors, and the like; pH normalizing solutions, such as buffers, saline, hyaluronic acid and the like; and tissue, such as micronized autologous and/or allogenic intervertebral disc, cartilage, or other therapeutic tissues. Embodiments of the devices and methods are described below with reference to FIGS. 1A-5C.

Figure 1B:
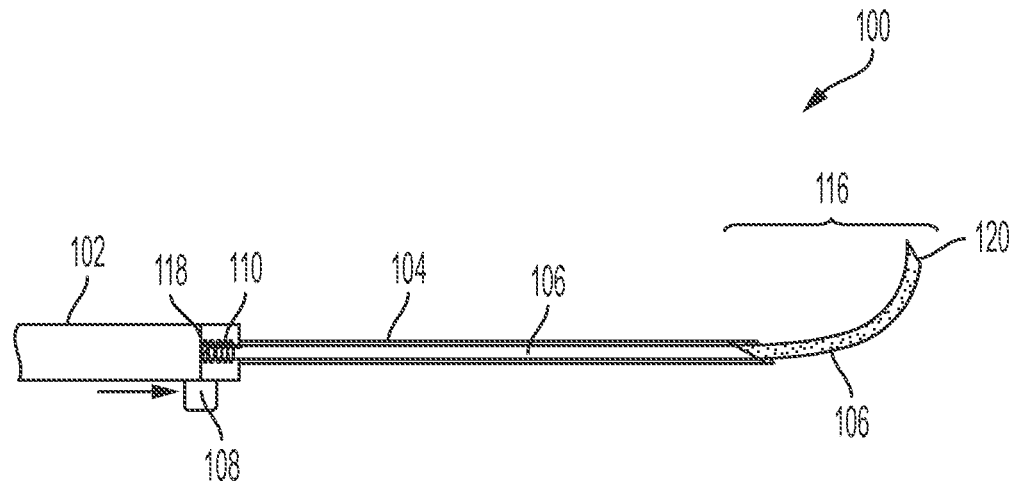
FIG. 1B illustrates a cross-sectional side view of an embodiment of the tool in a deployed position.

FIG. 1A illustrates a cross-sectional side view of an embodiment of a tool 100 in a default position 114. FIG. 1B illustrates a cross-sectional side view of an embodiment of the tool 100 in a deployed position 116.

In one or more embodiments, the tool 100 may include a handle 102, a first needle 104, and a second needle 106. The handle 102 is connected to a first needle 104 and may be configured to house at least a portion of a second needle 104. The handle 102 may be attached to a syringe or other device capable of storing the therapeutic materials and providing the therapeutic materials to the first needle 104 and/or the second needle 106.

The first needle 104 is configured to house at least a portion of the second needle 106. The first needle 104 may be an elongated rigid tube having an insertion end 112 positioned on an end opposite the end connected to the handle 102. The insertion end 112 of the first needle 104 may include a sharp and shallow beveled end. In one or more cases, an angle of the beveled end of the first needle 104 may be formed at 20 to 60 degrees, and more preferably 20 to 30 degrees. The first needle 104 may be formed out of a radio-opaque material, such as surgical grade stainless steel, or may be formed of a polymer that may be radiopaque or radiolucent to varying degrees, or the like. In one or more embodiments, the first needle 104 may be used to reach sub-ligamentous space between a longitudinal ligament and a vertebral body.

The second needle 106 may be an elongated flexible tube configured to retract and deploy from within the first needle 104. The insertion end 120 of the second needle 106 may include a tactile-tip end. The gauge of the second needle 106 may be of a variety of sizes capable of retracting and deploying from within the first needle 104, and more preferably, may be of the smallest gauge that allows for the delivery of the chosen therapeutic materials. In one or more embodiments, the second needle 106 is configured to enter an intervertebral disc. The second needle 106 may be configured to deliver the therapeutic materials to a location, such as a target intervertebral disc. The second needle 106 may be formed out of a shape memory alloy, such as, nitinol, or the like and may be configured to bend. In one or more cases, the second needle 106 is configured to curve in a direction opposite a switch 108 connected to the handle 102. By curving the second needle 106 in a direction opposite the switch 108, a user may use the switch 108 as a reference point to properly position and guide the second needle 106 to a location, such as a target intervertebral disc. In one or more other cases, the second needle 106 may be configured to curve in another direction respective to the switch 108, such as, a direction towards the switch 108, a direction perpendicular to the switch 108, an intercardinal direction (e.g., northeast, southeast, southwest, or northwest) respective to the switch 108, or at another angle relative to the position of the switch.

The tool 100 may be configured in a default position 114 (i.e., a retracted position) and a deployed position 116. For the cases in which the tool 100 is in a default position 114, the second needle 106 is housed within the first needle 104, such that the insertion end 120 of the second needle 106 may not extend beyond the opening of the insertion end 112 of the first needle 104. For the cases in which the tool 100 is in a deployed position 116, the second needle 106 is deployed from the insertion end 112 of the first needle 104. In a deployed position 116, the insertion end 120 of the second needle 106 may extend beyond the insertion end 112 of the first needle 104.

In one or more cases, the tool 100 may move between the default position 114 and the deployed position 116 via a spring system included in the handle 102. The spring system may be positioned within the handle 102. The spring system may include a spring 110, a switch 108, and a spring plate 118. The spring 110 may be positioned around a portion of the second needle 106 that is positioned within the handle 102. The switch 108 may be positioned on an outer surface of the handle 102. The switch 108 may be configured to move along the outer surface of the handle 102. The spring plate 118 may be coupled to the switch 108 and positioned within the handle 102. An end 106*a* of the second needle 106 may be coupled to the spring plate 118.

In one or more cases, as the switch 108 moves towards a proximal end 102*a* of the handle 102, the spring plate 118 moves concurrently with the switch 108, thereby moving the second needle 106 out of the first needle 104 and into a deployed position 116. The switch 108 may move along a track formed within the handle 102. As the switch 108 moves towards a proximal end 102*a* of the handle 102, the spring plate 118 compresses the spring 110 towards the proximal end 102*a* of the handle 102.

A user can control the deployed length of the second needle 106 based on the distance a user moves the switch 108 along the handle 102. For example, if the user moves the switch 108 a distance of 10 percent of the track, then the second needle 106 may be deployed at a length of 10 percent of the full deployed length of the second needle 106. In another example, if the user moves the switch 108 a distance of 100 percent of the track, then the second needle 106 may be fully deployed. In one or more cases, the track may include deployed length indicators to indicate a deployed distance of the second needle 106. For example, if the switch 108 aligns with a 10 percent indicator on the track, then the deployed length indicator may indicate that the second needle 106 may be deployed at a length of 10 percent of the full deployed length of the second needle 106. Once in the deployed position 116, the switch 108 may be configured to lock in place on the handle 102 in order to maintain the tool 100 in the deployed position 116 and facilitate the delivery of therapeutic materials. When retracting the switch 108, the spring may apply a force on the spring plate 118 to facilitate returning the tool to the default position 114. In one or more other cases, the spring may not be included in the spring system.

In one or more other embodiments, the tool 100 may be a triple-layer needle. The triple-layer needle may include an innermost needle, a middle needle, and an outermost needle. The outermost needle is configured to house the middle needle and the innermost needle. The middle needle is configured to house the innermost needle. The middle needle is configured to retract and deploy from the outermost needle. The innermost needle is configured to retract and deploy from the outermost needle and the middle needle. An insertion end of the outermost needle may include a blunt or tactile tip end for reaching and/or "feeling" the lateral margin of the posterior longitudinal ligament 304 and/or the anterior longitudinal ligament 302. An end of the middle needle may include a sharp beveled end similar to insertion end 112 that is configured to wedge under the posterior longitudinal ligament 304 and/or the anterior longitudinal ligament 302. The innermost needle may include one or more of the same features of the second needle 106.

Figure 2:
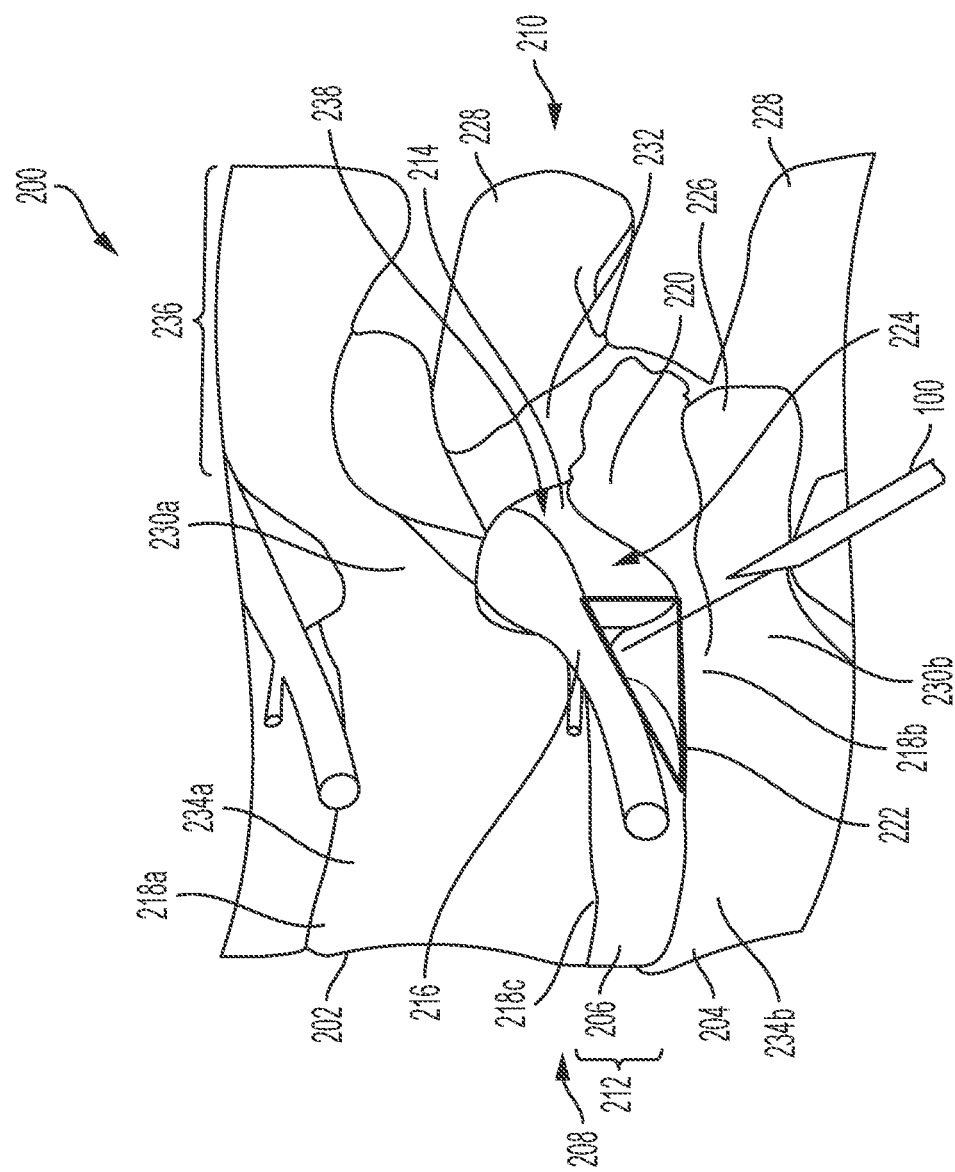
FIG. 2 is a lateral view of a section of vertebrae that illustrates an embodiment of a posterolateral or transforaminal approach to enter an intervertebral disc from a posterior portion or posterolateral portion of the intervertebral disc.
Figure 3A:
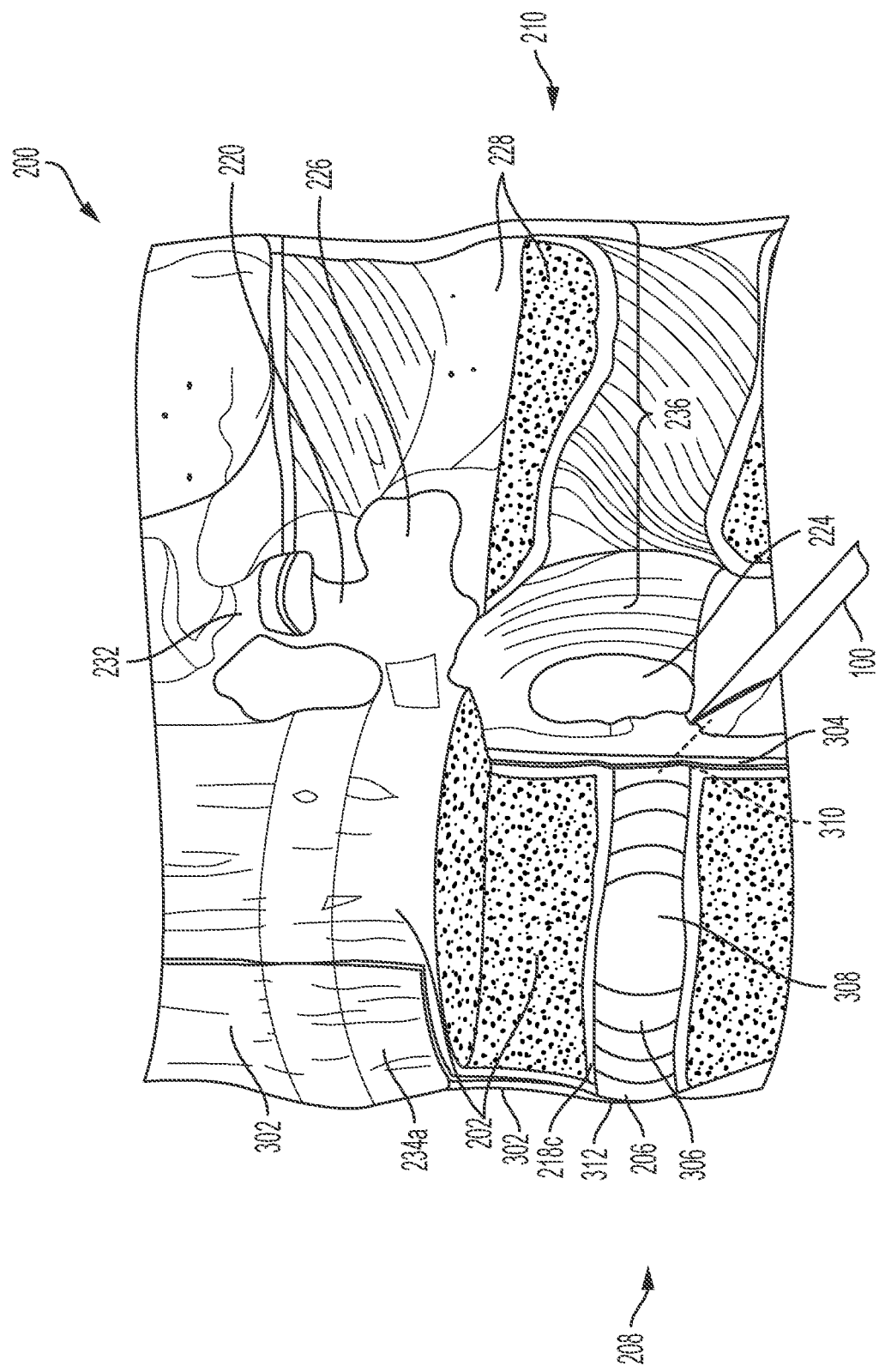
FIG. 3A is a partial cross-sectional view of the lateral view of the section of vertebrae that illustrates an embodiment of the posterolateral or transforaminal approach to the intervertebral disc.
Figure 3B:
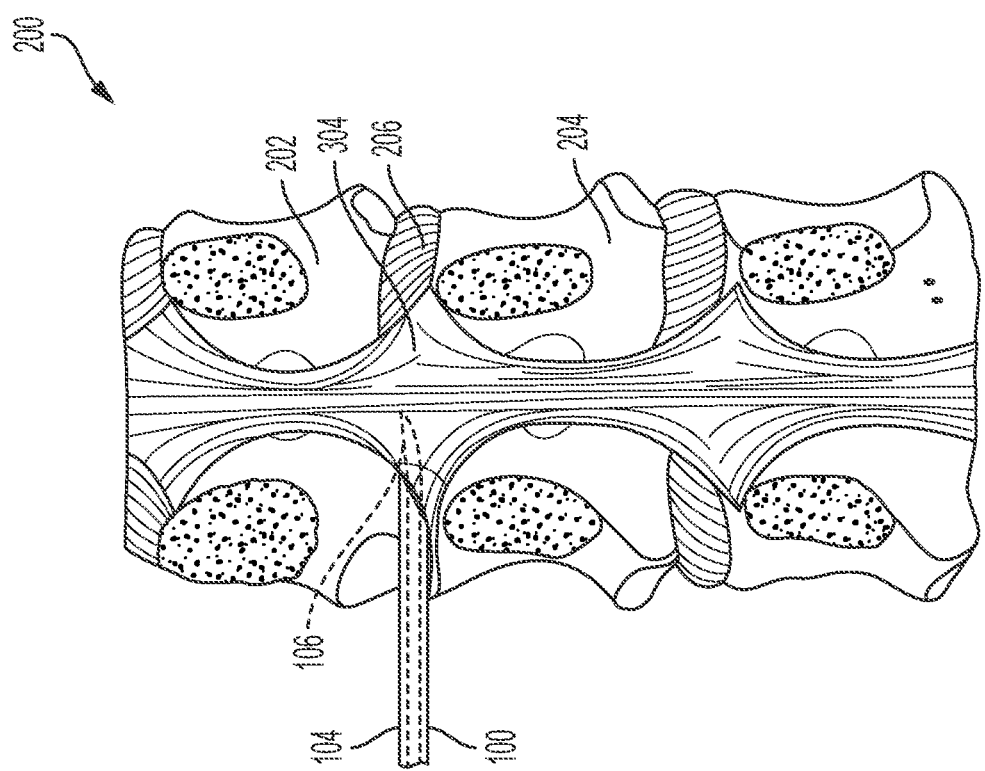
FIG. 3B is a posterior view of the section of vertebrae that illustrates an embodiment of the posterolateral or transforaminal approach to the intervertebral disc.

FIG. 2 is a lateral view of a section of vertebrae 200 that illustrates an embodiment of a posterolateral transforaminal approach to enter an intervertebral disc 206 from a posterior portion or a posterolateral portion of the intervertebral disc 206. FIG. 3A is a partial cross-sectional view of the lateral view of the section of vertebrae 200 that illustrates an embodiment of the posterolateral transforaminal approach to the intervertebral disc 206. FIG. 3B is a posterior view of the section of vertebrae 200 that illustrates an embodiment of the posterolateral transforaminal approach to the intervertebral disc 206. It is noted that the section of vertebrae 100, described in FIGS. 2-4B, relates to a lumbar section of a spine; however, it should be noted that the embodiments discussed herein can relate to other sections of the spine, such as the cervical and thoracic sections.

The vertebra 234*a* includes a vertebral body 202, which is located on the anterior side 208 of the vertebra 234*a*. The vertebral body 202 includes an endplate 218*a* located on the upper horizontal portion of the vertebral body 202 and an endplate 218*c* located on the lower horizontal portion of the vertebral body 202. Similarly, the vertebra 234*b* includes a vertebral body 204, which is located on the anterior side 208 of the vertebra 234*b*. The vertebral body 204 includes an endplate 218*b* located on the upper horizontal portion of the vertebral body 202 and an endplate 218*d* (shown in FIG. 3A) located on the lower horizontal portion of the vertebral body 202.

The vertebra 234*a* includes a posterior vertebral arch 236 located on the posterior side 210 of the vertebra 234*a*. The posterior vertebral arch 236 includes a spinous process 228, a lamina, left and right superior articular processes 220, left and right transverse processes 226, and right and left pedicles, such as left pedicles 230*a* and 230*b*. It is noted that the spinous process 228, left superior articular process 220, left transverse process 226 and left pedicles 230*a* and 230*b* are shown in FIGS. 2-4B, and the discussion herein describes the features of the left side of the spine; however, the discussion of the features is equally applicable to the right side of the spine. The lamina extends from an end of the spinal canal 238 to the spinous process 228. The left pedicle 230*a* is connected to the vertebral body 202 and extend outwards away from the vertebral body 202. The left superior articular process 220 is located between the lamina and the left pedicle 230*a*. The posterior vertebral arch 236 and the vertebral body 202 form the spinal canal 238, in which the spinal cord 214 passes through. Similarly, the vertebra 234*b* includes a posterior vertebral arch located on the posterior side 210 of the vertebra 234*b*, in which the posterior vertebral arch includes one or more features similar to the posterior vertebral arch 236.

An intervertebral foramen 224 may be a bony hollow archway created by the pedicle 230*a* of the vertebra 234*a* and the pedicle 230*b* of the vertebra 234*b*. The intervertebral foramen 224 creates a passageway for a spinal nerve root 216 to pass from the spinal cord 214 through the intervertebral foramen 224 and out towards a respective part of the body, such as an organ, muscles, and/or sensory structures of the body. A Kambin's Triangle 222 is formed in a region of the intervertebral foramen 224 beneath the spinal nerve root 216, anterior to the spinal cord 214, and devoid of vascular structures in an anatomically typical patient.

An intervertebral disc 206 is located within the intradiscal space 212 between two adjacent vertebral bodies, such as vertebral body 202 and vertebral body 204. The intradiscal space 212 is a region between the two adjacent vertebral bodies in the vertebral column. The intervertebral disc 206 connects the two adjacent vertebral bodies and allows movement of the section of vertebrae 200. The intervertebral disc 206 is composed of an annulus fibrosus 306 (the "annulus 306") and the nucleus pulposus 308 (the "nucleus 308"). The annulus 306 surrounds the nucleus 308 and is connected to the vertebral endplates 218c and 218b.

A posterior longitudinal ligament 304 extends along the posterior surfaces of each of the vertebra in a longitudinal direction of the spine. The width of posterior longitudinal ligament 304 at the intervertebral disc space 212 is greater than the width of the posterior longitudinal ligament 304 at an area over a vertebral body, such as vertebral body 202. In one or more cases, the sub-ligamentous space 310 may be the area where the posterior longitudinal ligament 304 interfaces with the outer surface of the intervertebral disc 206 and/or the annulus 306. In one or more other cases, the sub-ligamentous space 310 of the posterior longitudinal ligament 304 may be the area located in between the outer surface of a vertebral body, such as vertebral body 202, and an inner surface of the posterior longitudinal ligament 304.

An anterior longitudinal ligament 302 extends along the anterior surfaces of the vertebra in a longitudinal direction of the spine. The width of anterior longitudinal ligament 302 at the intervertebral disc space 212 is greater than the width of the anterior longitudinal ligament 302 at an area over a vertebral body, such as vertebral body 202. In one or more cases, the sub-ligamentous space 312 may be the area where the anterior longitudinal ligament 302 interfaces with the outer surface of the intervertebral disc 206 and/or the annulus 306. In one or more other cases, the sub-ligamentous space 312 of the anterior longitudinal ligament 302 may be the area located in between the outer surface of a vertebral body and an inner surface of the anterior longitudinal ligament 304.

In one or more embodiments, the tool 100 may penetrate the target intervertebral disc, such as intervertebral disc 206, via the sub-ligamentous space 310. That is, the tool 100 may reach the nucleus 308 or other inner structures of the intervertebral disc 206 by entering the annulus 306 beneath the posterior longitudinal ligament 304 or the anterior longitudinal ligament 302.

In one or more cases, to begin the posterolateral or transforaminal approach as illustrated in FIGS. 2-3B, the user may administer light anesthesia to the injection site. The light anesthesia may allow a patient to provide feedback to the user to facilitate safe passage of the first needle 104 of the tool 100 beneath the spinal nerve 216 and underneath the lateral margin of the posterior longitudinal ligament 304 and into the sub-ligamentous space 310. For example, the patient may inform the user if the patient is feeling paresthesia or discomfort, which would indicate to the user that the tool 100 may have contacted a portion of the spinal nerve 216.

In one or more embodiments, to enter a posterior portion or a posterolateral portion of the intervertebral disc 206 via the posterolateral or transforaminal approach, a user inserts the tool 100, being configured in a default position 114, into a portion of the patient's back at or near the target disc. Using image-guidance, such as viewing an x-ray of the injection site and area surrounding the target disc, the user may guide the tool 100 through an inferoanterior aspect of the intervertebral foramen 224 at the level of the target disc. That is, the user may guide the tool 100 through the Kambin's Triangle 222. In one or more embodiments, a nerve monitoring sensor may be included on the insertion end 112 to detect whether the tool 100 contacted the spinal cord 214 and/or spinal nerve root 216. The trajectory of the tool 100 may remain anterior to the spinal cord 214. The user may guide the insertion end 112 of the first needle 104 from a posterolateral side of the intervertebral disc 206 to the sub-ligamentous space 310. The insertion end 112 may be parallel to the interface of the posterior longitudinal ligament 304 and the outer surface of the intervertebral disc 206. The user may guide the insertion end 112 of the first needle 104 in the sub-ligamentous space 310 (i.e., beneath the posterior longitudinal ligament 304) up to one half the width of the posterior longitudinal ligament 304 while remaining in the sub-ligamentous space 310. For example, from a posterolateral side of the intervertebral disc 206, the user may guide the insertion end 112 of the first needle 104 beneath the posterior longitudinal ligament 304 and towards the midline of the posterior longitudinal ligament 304. In one or more embodiments, the user may guide the insertion end 112 of the first needle 104 in the sub-ligamentous space 310, preferably without creating needle tracks in the posterior longitudinal ligament 304. In one or more embodiments, the user may guide the insertion end 112 of the first needle 104 in the sub-ligamentous space 310 without moving the lateral margin of the posterior longitudinal ligament 304 or by moving the lateral margin of the posterior longitudinal ligament 304 with a retractor.

The user may optionally rotate the tool 100 to position the insertion angle of the second needle 106 into the intervertebral disc 206. In one or more cases, the user may rotate the tool 100 within the sub-ligamentous space 310 to position the insertion angle of the second needle 106. The user may use the switch 108 as a guide to align the insertion angle of the second needle 106. For example, for the cases in which the user inserts the first needle 104 into the sub-ligamentous space 310 and the opening of the insertion end 112 faces towards the posterior longitudinal ligament 304, the user may rotate the tool 100 such that the switch 108 may be positioned 180° from an angle of curvature of the second needle 106 in a deployed position 116. That is, the switch 108 may be positioned in a manner to indicate that the opening of the insertion end 112 of the first needle 104 faces in a direction towards the annulus 306. In one or more other cases, a marking, such as an arrow or dot, may be positioned on the handle 102 in a manner to indicate that the opening of the insertion end 112 of the first needle 104 faces in a direction towards the annulus 306.

Having positioned the insertion angle of the second needle 106, the user may configure the tool 100 into a deployed position 116. To configure the tool 100 into the deployed position 116, the user may move the switch 108 along the outer surface of the handle 102, thereby deploying the second needle 106 out of the first needle 104. The deployed second needle 106 may breach at least a portion of the annulus 306. In one or more embodiments, the insertion end 120 of the second needle 106 is configured to enter at least a portion of the nucleus 308 for the cases in which the switch 108 is moved to a full deployed length (e.g., the switch 108 being moved a distance of 100 percent of the track within the handle 102) or near fully deployed length (e.g., the switch 108 being moved a distance of 65 percent to 99 percent of the track within the handle 102) of the second needle 106. Having entered at least a portion of the nucleus 308, the user may administer the therapeutic material to the nucleus 308. In one or more embodiments, the insertion end 120 of the second needle 106 is configured to be positioned within a portion of the annulus 306 for the cases in which the switch 108 is moved partially into the deployed position 116 (e.g., the switch 108 being moved a distance of 10 percent to 64 percent of the track within the handle 102), thereby allowing the user to administer the therapeutic material intra-annularly. Once the insertion end 120 of the second needle 106 is positioned within the intervertebral disc 206, the therapeutic material is delivered, e.g., by depressing a plunger, such as plunger 626*a* in FIG. 6A, attached to the syringe, to the intervertebral disc 206 via the second needle 106.

Subsequent to completing the delivery of the therapeutic material, the user may move the switch 108 into the default position 114 to retract the second needle 106 into the first needle 104. When the tool 100 is configured in the default position 114, the first needle 104 can be withdrawn from the patient. The user may withdraw the first needle 104 along the same path in front of the spinal cord 214 and through the Kambin's Triangle 222.

In one or more embodiments, by removing the first needle 104 from the sub-ligamentous space 310, the posterior longitudinal ligament 304 may seal or partially seal the needle track, thereby acting as an endogenous bandage to allow for healing of the needle track and to ensure that all or substantially all of the dose of therapeutic material is retained within the intervertebral disc 206. For the cases in which the second needle 106 fully penetrated the annulus 306 and entered the nucleus 308, the stiff collagenous structures of the posterior longitudinal ligament 304 may act to block the full-thickness transannular needle track created by the second needle 106.

Figure 4A:
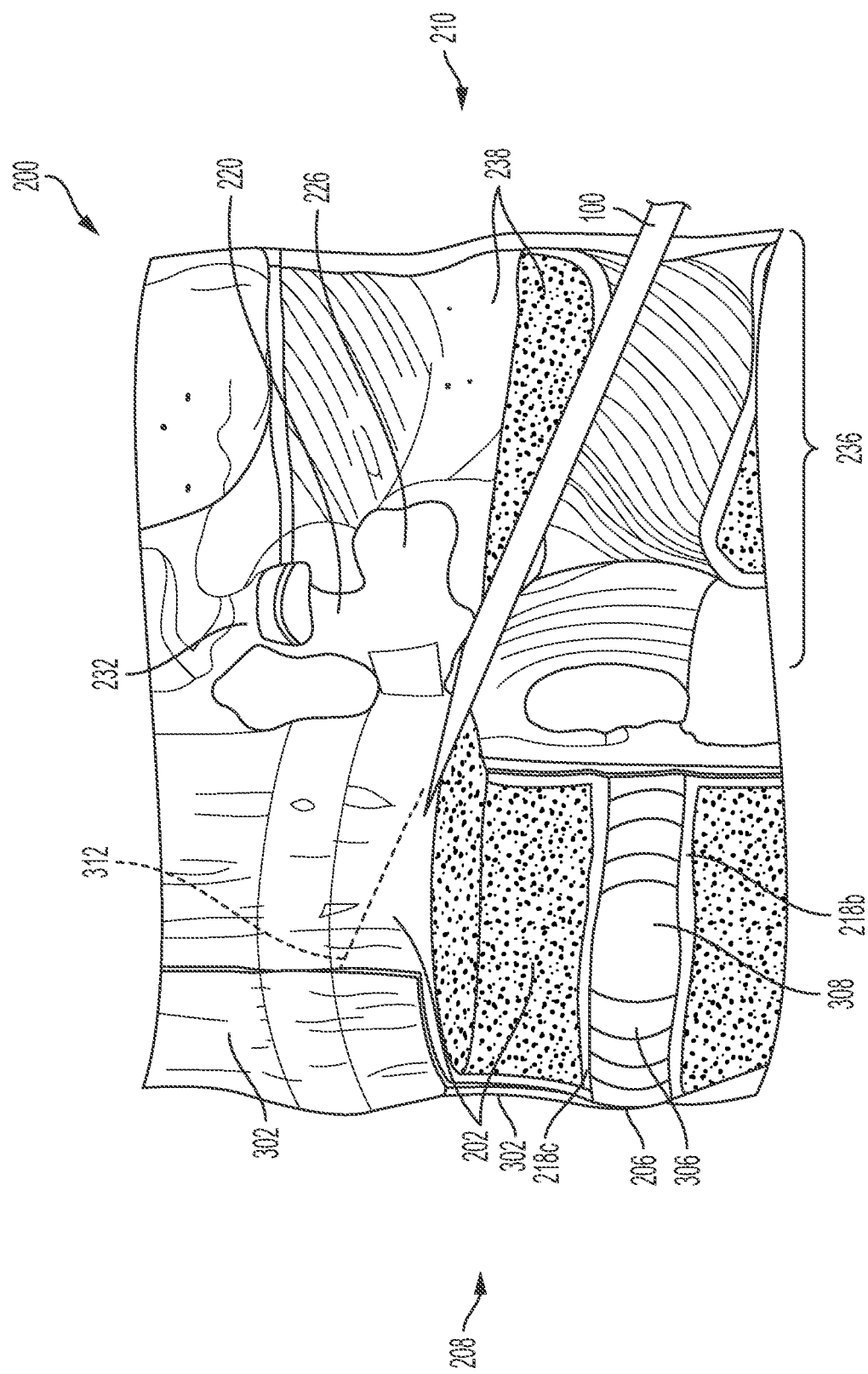
FIG. 4A is a partial cross-sectional view of the lateral view of the section of vertebrae that illustrates an embodiment of an approach, via an anterior longitudinal ligament, (the "ALL approach") to enter the intervertebral disc from an anterolateral portion or an anterior portion of the intervertebral disc.
Figure 4B:
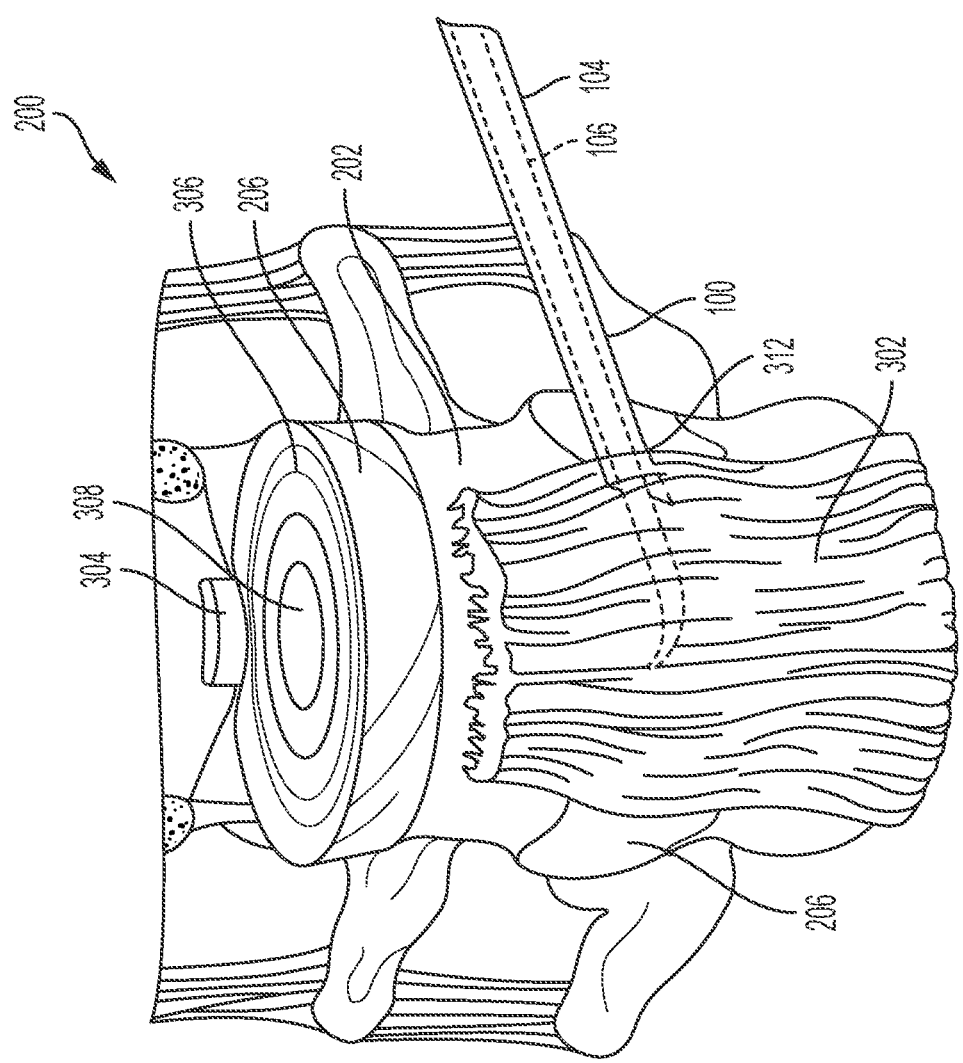
FIG. 4B is an anterior view of the section of vertebrae that illustrates an embodiment of the ALL approach to the intervertebral disc.

FIG. 4A is a partial cross-sectional view of the lateral view of the section of vertebrae 200 that illustrates an embodiment of an approach, via the anterior longitudinal ligament 302, (the "ALL approach") to enter the intervertebral disc 206 from an anterolateral portion or an anterior portion of the intervertebral disc 206. FIG. 4B is an anterior view of the section of vertebrae 200 that illustrates an embodiment of the ALL approach to the intervertebral disc 206.

In one or more cases, to begin the ALL approach as illustrated in FIGS. 4A-4B, the user may administer light anesthesia to the injection site. The light anesthesia may allow a patient to provide feedback to the user to facilitate safe passage of the first needle 104 of the tool 100 underneath the lateral margin of the anterior longitudinal ligament 302 and into the sub-ligamentous space 312. For example, the patient may inform the user if the patient is feeling paresthesia or discomfort, which would indicate to the user that the tool 100 may have contacted a portion of the spinal nerve 216.

In one or more embodiments, to enter an anterolateral portion or an anterior portion of the intervertebral disc 206 via the ALL approach, a user inserts the tool 100, being configured in a default position 114, into a portion of the patient's back at or near the target disc. Using image-guidance, such as viewing an x-ray of the injection site and area surrounding the target disc, the user may guide the tool 100, in particular the insertion end 112 of the first needle 104, from a posterolateral side of the intervertebral disc 206 to the sub-ligamentous space 312. The insertion end 112 may be parallel to the interface of the anterior longitudinal ligament 302 and the outer surface of the intervertebral disc 206. The user may guide the insertion end 112 of the first needle 104 in the sub-ligamentous space 312 (i.e., beneath the anterior longitudinal ligament 302) up to one half the width of the anterior longitudinal ligament 302 while remaining in the sub-ligamentous space 312. In one or more embodiments, the user may guide the insertion end 112 of the first needle 104 in the sub-ligamentous space 312, preferably without creating needle tracks in the posterior longitudinal ligament 304. In one or more embodiments, the user may guide the insertion end 112 of the first needle 104 in the sub-ligamentous space 312 without moving the lateral margin of the anterior longitudinal ligament 302 or by moving the lateral margin of the anterior longitudinal ligament 302 with a retractor.

Similar to positioning the insertion angle of the second needle 106 in the posterior transforaminal approach, the user may optionally rotate the tool 100 to position the insertion angle of the second needle 106 into the intervertebral disc 206. In one or more cases, the user may rotate the tool 100 within the sub-ligamentous space 312 to position the insertion angle of the second needle 106. The user may use the switch 108 as a guide to align the insertion angle of the second needle 106. In one or more other cases, a marking, such as an arrow or dot, may be positioned on the handle 102 in a manner to indicate that the opening of the insertion end 112 of the first needle 104 faces in a direction towards the annulus 306.

Having positioned the insertion angle of the second needle 106, the user may configure the tool 100 into a deployed position 116. To configure the tool 100 into the deployed position 116, the user may move the switch 108 along the outer surface of the handle 102, thereby deploying the second needle 106 out of the first needle 104. The deployed second needle 106 may breach at least a portion of the annulus 306. In one or more embodiments, the insertion end 120 of the second needle 106 is configured to enter at least a portion of the nucleus 308 for the cases in which the switch 108 is moved to a full deployed length (e.g., the switch 108 being moved a distance of 100 percent of the track within the handle 102) or near fully deployed length (e.g., the switch 108 being moved a distance of 65 percent to 99 percent of the track within the handle 102) of the second needle 106. Having entered at least a portion of the nucleus 308, the user may administer the therapeutic material to the nucleus 308. In one or more embodiments, the insertion end 120 of the second needle 106 is configured to be positioned within a portion of the annulus 306 for the cases in which the switch 108 is moved partially into the deployed position 116 (e.g., the switch 108 being moved a distance of 10 percent to 64 percent of the track within the handle 102), thereby allowing the user to administer the therapeutic material intra-annularly. Once the insertion end 120 of the second needle 106 is positioned within the intervertebral disc 206, the therapeutic material is delivered, e.g., by depressing a plunger, such as plunger 626*a* in FIG. 6A, attached to the syringe, to the intervertebral disc 206 via the second needle 106.

Subsequent to completing the delivery of the therapeutic material, the user may move the switch 108 into the default position 114 to retract the second needle 106 into the first needle 104. When the tool 100 is configured in the default position 114, the first needle 104 can be withdrawn from the patient. The user may withdraw the first needle 104 along the same path in which the first needle 106 entered the sub-ligamentous space 312. In one or more embodiments, by removing the first needle 104 from the sub-ligamentous space 312, the anterior longitudinal ligament 302 may seal or partially seal the needle track, thereby acting as an endogenous bandage to allow for healing of the needle track and to ensure that all or substantially all of the dose of the therapeutic material is retained within the intervertebral disc 206. For the cases in which the second needle 106 fully penetrated the annulus 306 and entered the nucleus 308, the stiff collagenous structures of the anterior longitudinal ligament 302 may act to block the full-thickness transannular needle track created by the second needle 106.

In one or more other embodiments, to enter an anterolateral portion or an anterior portion of the intervertebral disc 206 via another ALL approach, a user may insert a curved tool into an anterior portion or anterolateral portion of a patient's abdomen at a level near the target disc. The curved tool may include one or more of the same features as tool 100. However, the outer needle of the curved tool has having a curved shape as opposed to the straight shape of the first needle 104. The curved shape of the outer needle may facilitate entry into the sub-ligamentous space 312 from an anterolateral side of the intervertebral disc 206. When inserting the curved tool into the patient, the curved tool may be positioned such that the curved tool curves towards the intervertebral disc 206. Once the user guides the curved tool to reach the sub-ligamentous space 312, the user may guide the outer needle of the curved tool in an arc-like manner and/or curving trajectory into the sub-ligamentous space 312. In one or more embodiments, the inner needle of the curved tool may include one or more of the same features as the second needle 106. The inner needle may be configured to curve away from the curvature of the outer needle, thereby forming an "S" like shape when the curved tool is configured in a deployed position. When being configured in a deployed position, the inner needle may enter the intervertebral disc 206 from an anterolateral portion or an anterior portion of the intervertebral disc 206. In a deployed position, the inner needle may breach at least a portion of the annulus 306. In one or more embodiments, the insertion end of the inner needle is configured to enter at least a portion of the nucleus 308 for the cases in which the switch of the curved tool is moved to a full deployed length.

Figure 5A:
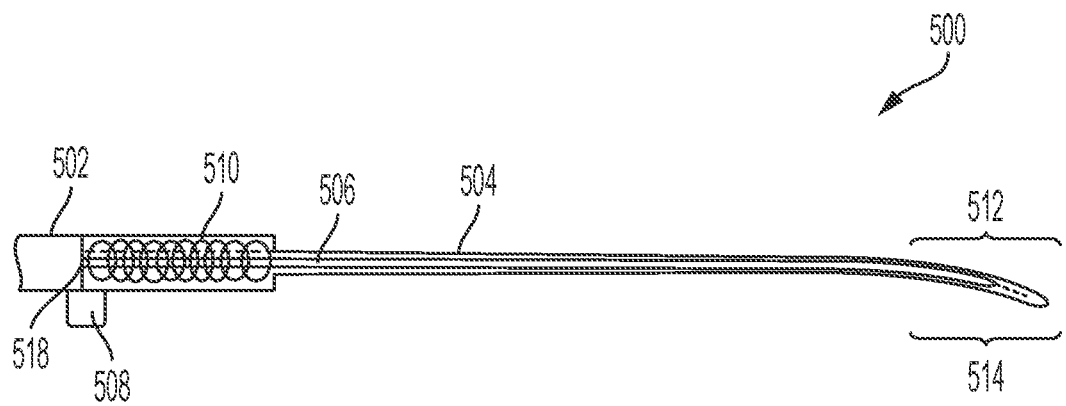
FIG. 5A illustrates a cross-sectional side view of an embodiment of a tool in a default position.
Figure 5B:
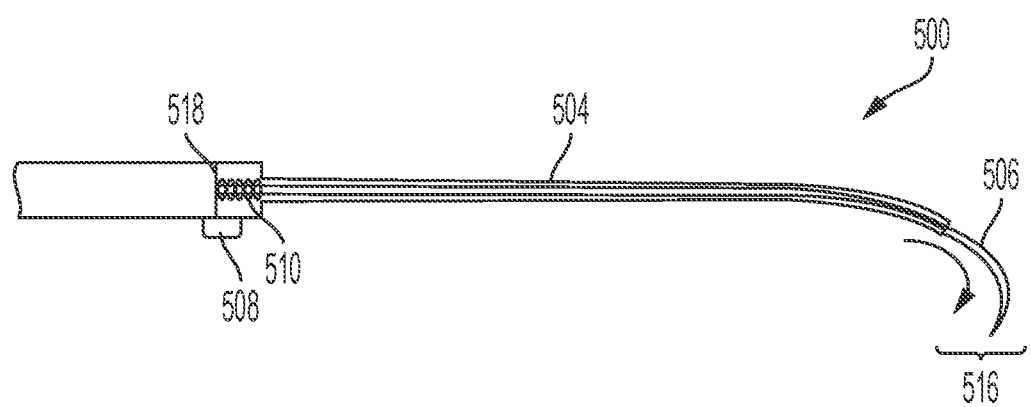
FIG. 5B illustrates a cross-sectional side view of an embodiment of the tool in a deployed position.
Figure 5C:
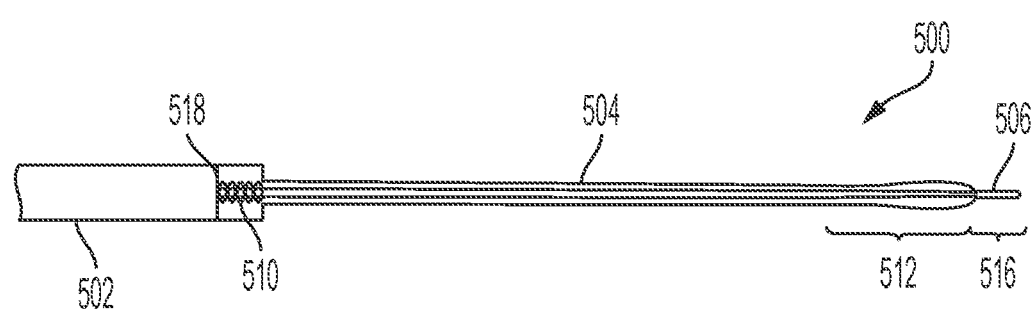
FIG. 5C illustrates a cross-sectional top view of an embodiment of the tool in a deployed position.

FIG. 5A illustrates a cross-sectional side view of an embodiment of a tool 500 in a default position 514. FIG. 5B illustrates a cross-sectional side view of an embodiment of the tool 500 in a deployed position 516. FIG. 5C illustrates a cross-sectional top view of an embodiment of the tool 500 in a deployed position 516.

In one or more embodiments, the tool 500 may include a handle 502, a first needle 504, and a second needle 506. The handle 502 is connected to the first needle 504 and may be configured to house at least a portion of the second needle 504. The handle 502 may be attached to a syringe or other device capable of storing the therapeutic materials and providing the therapeutic materials to the first needle 504 and/or the second needle 506. In one or more embodiments, the tool 500 may be used in place of tool 100 for either of the posterolateral or transforaminal approach to enter the intervertebral disc 206 from a posterior portion or posterolateral portion of the intervertebral disc 206 or the ALL approach to enter the intervertebral disc 206 from an anterolateral portion or an anterior portion of the intervertebral disc 206 described above. The discussion of FIG. 5 herein discusses an example implementation of the posterolateral or transforaminal approach entering the intervertebral disc 206 from a posterior portion or posterolateral portion of the intervertebral disc 206.

It is noted that the handle 502, the second needle 506, and a spring system, including a spring 510, a switch 508, and a spring plate 518, include one or more of the same features as described with respect to the handle 102, the second needle 106, and a spring system, including a spring 110, a switch 108, and a spring plate 118. Accordingly, a description of these features is not repeated.

The first needle 504 is configured to house at least a portion of the second needle 506. The first needle 504 may be an elongated rigid tube having an insertion end 512 positioned on an end opposite the end connected to the handle 502. The insertion end 512 of the first needle 504 may be a flattened tissue elevator configured to separate the anterior longitudinal ligament 302 and/or posterior longitudinal ligament 304 from a vertebral body. For example, the flattened tissue elevator may be formed in a shape similar to an insertion end of a Penfield Dissector No. 4. The insertion end 512 may facilitate blunt separation of the anterior longitudinal ligament 302 and/or posterior longitudinal ligament 304 from the annulus 306. The insertion end 512 may be formed in a concave shape. The first needle 504 may be formed out of a radio-opaque material, such as surgical grade stainless steel, or may be formed of a polymer that may be radiopaque or radiolucent to varying degrees, or the like. In one or more embodiments, the first needle 504 may be used to reach the sub-ligamentous space. In one or more embodiments, the second needle 506 may be configured to curve with the curvature of the insertion end 512. That is, the second needle 506 may curve with the concave shape of the insertion end 512, such that the path of the second needle 506 may follow a portion of the path of the concaved shaped end of the first needle 504.

The tool 500 may be configured in a default position 514 (i.e., a retracted position) and a deployed position 516. For the cases in which the tool 500 is in a default position 514, the second needle 506 is housed within the first needle 504, such that the insertion end 520 of the second needle 506 may not extend beyond the opening of the insertion end 512 of the first needle 504. For the cases in which the tool 500 is in a deployed position 516, the second needle 506 is deployed from the insertion end 512 of the first needle 504. In a deployed position 516, the insertion end 520 of the second needle 506 may extend beyond the insertion end 512 of the first needle 504.

In one or more embodiments, to enter a posterior portion or a posterolateral portion of the intervertebral disc 206, a user inserts the tool 500, being configured in a default position 514, into a portion of the patient's back at or near the target disc. Using image-guidance, such as viewing an x-ray of the injection site and area surrounding the target disc, the user may guide the tool 500 through an inferoanterior aspect of the intervertebral foramen 224 at the level of the target disc. That is, the user may guide the tool 500 through the Kambin's Triangle 222. The trajectory of the tool 500 may remain anterior to the spinal cord 214. The user may guide the insertion end 512 of the first needle 104 to the lateral margin of the posterior longitudinal ligament 304 and separate the lateral margin of the posterior longitudinal ligament 304 from the intervertebral disc 206. The insertion end 512 of the first needle 504 may be configured to facilitate insertion between anterior longitudinal ligament 302 and the annulus 306 of the intervertebral disc 206. The insertion end 512 of the first needle 504 may be inserted between the two types of tissue, and through a rocking motion, can split the two tissues apart and be advanced into the sub-ligamentous space 312. In one or more cases, user may guide the insertion end 512 of the first needle 104 from a posterolateral side of the intervertebral disc to the lateral margin of the posterior longitudinal ligament 304. The insertion end 512 may be parallel to the interface of the posterior longitudinal ligament 304 and the outer surface of the intervertebral disc 206. When separating the lateral margin of the posterior longitudinal ligament 304 from the target intervertebral disc 206, the insertion end 512 may curve away from the annulus 306.

Having separated the lateral margin of the posterior longitudinal ligament 304 from the target intervertebral disc 206, the user may rotate the insertion end 512 to curve towards the annulus 306 to facilitate insertion of the second needle 506 into the sub-ligamentous space 310. The user may position the insertion angle of the second needle 506 in a similar manner as positioning the insertion angle of the second needle 106 and using the switch 108 as a guide. The user may configure the tool 500 into a deployed position 516. The user may deploy the second needle 506 in a similar manner as described with respect to deploying the second needle 106. Similar to the switch 108, the user may move the switch 508 along the handle 502 to control the depth of the penetration of the second needle 506, which may range from shallow intra-annular administration of the therapeutic materials to full-thickness penetration of the annulus 306 and deposition of the therapeutic material into the nucleus 308.

Subsequent to completing the delivery of the therapeutic material, the user may move the switch 508 into the default position 514 to retract the second needle 506 into the first needle 504. When the tool 500 is configured in the default position 514, the first needle 504 can be withdrawn from the patient. The user may withdraw the first needle 504 along the same path in front of the spinal cord 214 and through the Kambin's Triangle 222. In one or more embodiments, by removing the first needle 504 from the sub-ligamentous space 310, the posterior longitudinal ligament 304 may seal or partially seal the needle track, thereby acting as an endogenous bandage to allow for healing of the needle track and to ensure that all or substantially all of the dose of the therapeutic material is retained within the intervertebral disc 206. For the cases in which the second needle 506 fully penetrated the annulus 306 and entered the nucleus 308, the stiff collagenous structures of the posterior longitudinal ligament 302 may act to block the full-thickness transannular needle track created by the second needle 506.

Figure 6A:
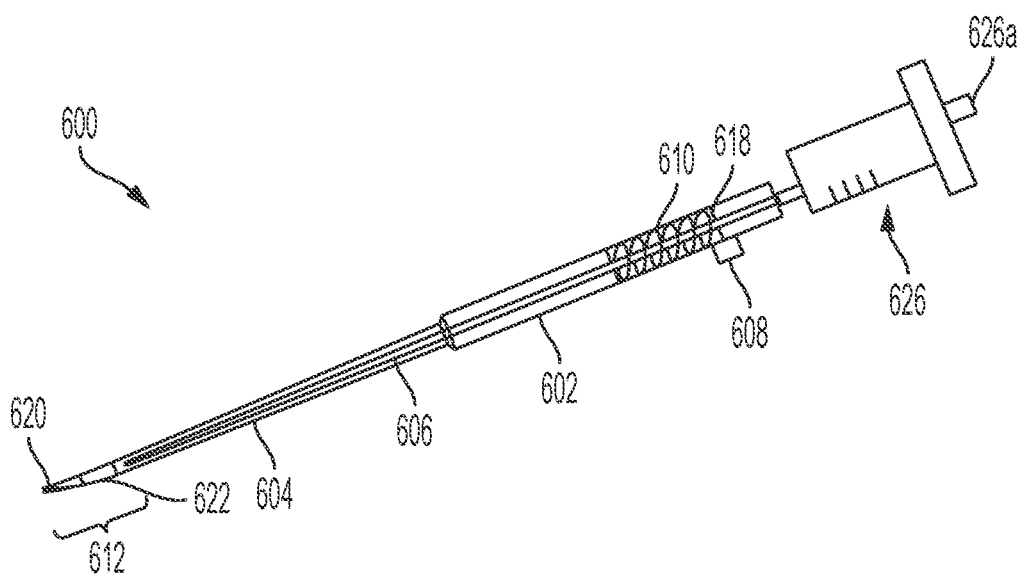
FIG. 6A illustrates a cross-sectional side view of an embodiment of a tool in a default position.
Figure 6B:
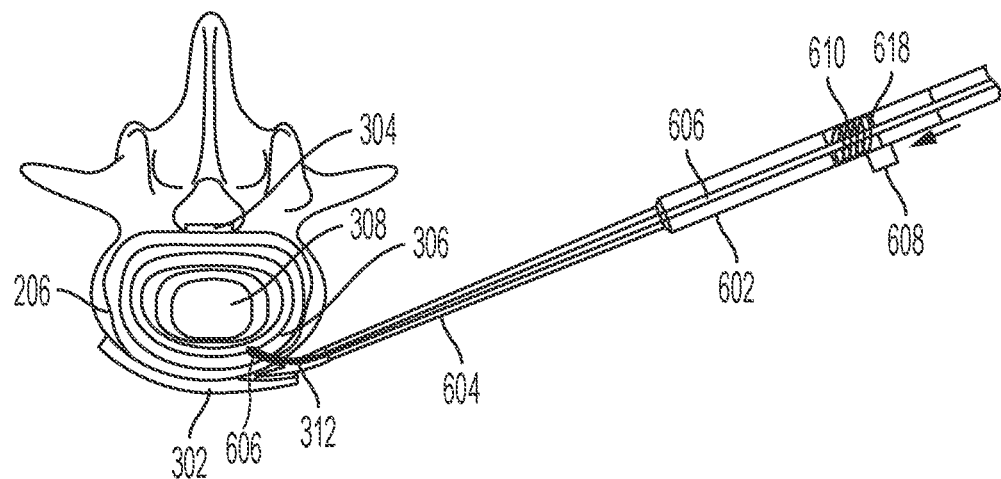
FIG. 6B illustrates a cross-sectional side view of an embodiment of the tool in a deployed position.
Figure 6D:
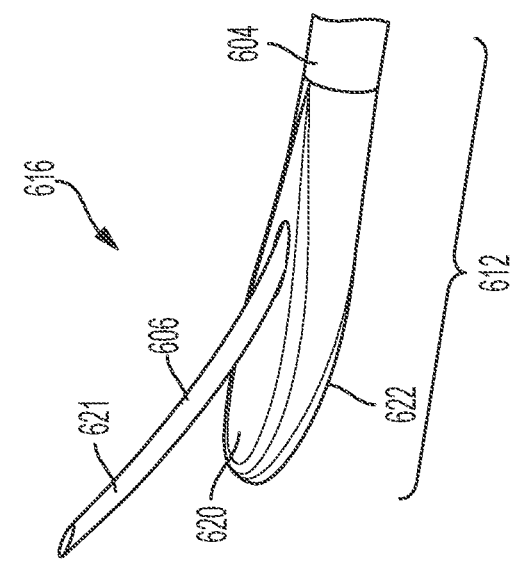
FIG. 6D illustrates an isometric view of a second needle deployed from the concave side of the insertion end of the tool.
Figure 6E:
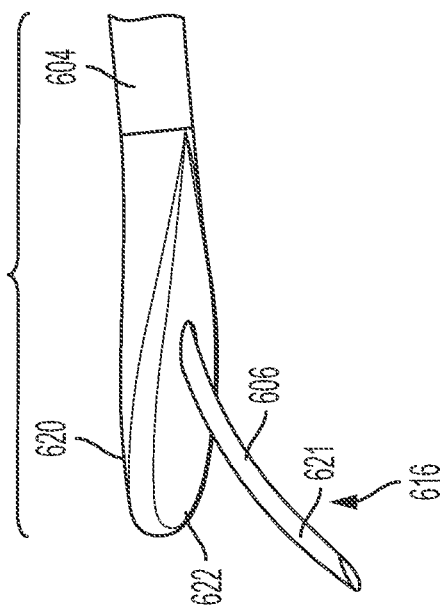
FIG. 6E illustrates an isometric view of the second needle being deployed from the concave side of the insertion end of the tool.
Figure 6C:
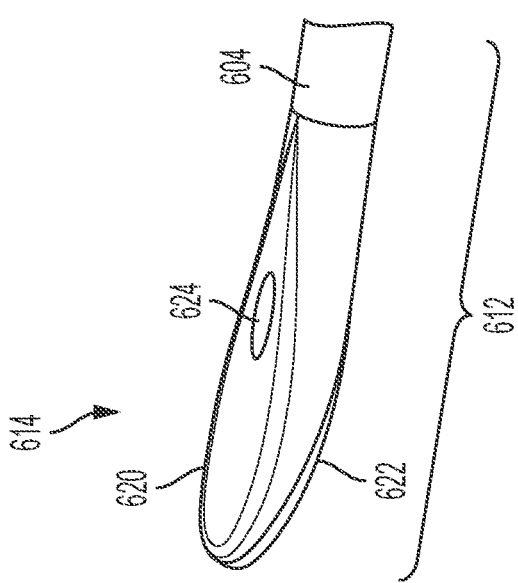
FIG. 6C illustrates an isometric view of a concave side of the insertion end of the tool in default position.

FIG. 6A illustrates a cross-sectional side view of an embodiment of a tool 600 in a default position 614. FIG. 6B illustrates a cross-sectional side view of an embodiment of the tool 600 in a deployed position 616. FIG. 6C illustrates an isometric view of a concave side 620 of an insertion end 612 of the tool 600 in default position 614. FIG. 6D illustrates an isometric view of a second needle 606 deployed from the concave side 620 of the insertion end 621 of the tool 600. FIG. 6E illustrates an isometric view of the second needle 606 being deployed from the convex side 622 of the insertion end 612 of the tool 600.

In one or more embodiments, the tool 600 may include a handle 602, a first needle 604, and the second needle 606. The handle 602 is connected to the first needle 604 and may be configured to house at least a portion of the second needle 606. The handle 602 may be attached to a syringe 626 or other device capable of storing the therapeutic materials and providing the therapeutic materials to the first needle 604 and/or the second needle 606. A plunger 626a may be depressed towards the syringe 626 thereby creating pressure within the syringe 626 and moving the therapeutic material out of the second needle 606. In one or more embodiments, the tool 600 may be used in place of tool 100 for either of the posterolateral or transforaminal approach to enter the intervertebral disc 206 from a posterior portion or posterolateral portion of the intervertebral disc 206 or the ALL approach to enter the intervertebral disc 206 from an anterolateral portion or an anterior portion of the intervertebral disc 206 described above. The discussion of FIG. 6 herein discusses an example implementation of the ALL approach to enter the intervertebral disc 206 from an anterolateral portion or an anterior portion of the intervertebral disc 206.

It is noted that the handle 602, the second needle 606, and a spring system, including a spring 610, a switch 608, and a spring plate 618, include one or more of the same features as described with respect to the handle 102, the second needle 106, and a spring system, including a spring 110, a switch 108, and a spring plate 118. Accordingly, a description of these features is not repeated.

The first needle 604 is configured to house at least a portion of the second needle 606. The first needle 604 may be an elongated rigid tube having an insertion end 612 positioned on an end opposite the end connected to the handle 602. The insertion end 612 of the first needle 604 may be a flattened tissue elevator configured to separate the anterior longitudinal ligament 302 and/or posterior longitudinal ligament 304 from a vertebral body. For example, the flattened tissue elevator may be formed in a shape similar to an insertion end of a Penfield Dissector No. 4. The insertion end 612 may facilitate blunt separation of the anterior longitudinal ligament 302 and/or posterior longitudinal ligament 304 from the annulus 306.

The tool 600 may include a cannula 624 positioned within at least a portion of the first needle 604 and/or at least a portion of the handle 602. The second needle 606 may reside within the cannula 624, thereby providing a track for the second needle 606 to deploy and retract from the first needle 604. The cannula 624 may be configured to protrude into at least a portion of the concave side 620 or at least a portion of the convex side 622. In one or more cases, the distal end of the cannula 624 may be curved, such that the second needle 606 is deployed on a curved path from the insertion end 612. In one or more other cases, the distal end of the cannula 624 may be straight, such that the second needle 606 is deployed on a straight path from the insertion end 612. The second needle 606 may be flexible to accommodate curves within the cannula 624. In one or more cases, the insertion end 612 of the tool 600 may include a concave side 620 and a convex side 622 disposed on opposite sides from one another on the insertion end 612 of the first needle 604. In one or more other cases, the insertion end 612 may include flat surfaces, in place of the concave surface of the concave side 620 and the convex surface of the convex side 622, disposed on opposite sides from one another on the insertion end 612.

In one or more cases, the insertion end 612 of the first needle 604 may be configured, such that the second needle 606 may deploy from either the concave side 620, as shown in FIG. 6D, or from the convex side 622, as shown in FIG. 6E. For the cases in which the second needle 606 is configured to deploy from the concave side 620, a distal end of the cannula 624 may be positioned towards the concave side 620, as shown in FIG. 6C. For the cases in which the second needle 606 is configured to deploy from the convex side 622, the distal end of the cannula 624 may be positioned towards the convex side 622. In one or more cases, the tool 600 may be configured, such that a user can selectively deploy the second needle 606 from the concave side 620 or from the convex side 622. For the cases in which second needle 606 can be selectively deployed from either the concave side 620 or the convex side 622, the cannula 624 may be formed to have two distal ends branching from the main body of the cannula 624, in which the cannula 624 may formed in a "Y" or branch-like shape. One distal branched end of the cannula 624 may be positioned towards the concave side 620, and the other distal branched end of the cannula 624 may be positioned towards the convex side 622. The user may selectively deploy the second needle 606 to either the distal branched end of the cannula 624 on the concave side 620 or to the distal branched end of the cannula 624 on the convex side 622.

The first needle 604 may be formed out of a radio-opaque material, such as surgical grade stainless steel, or may be formed of a polymer that may be radiopaque or radiolucent to varying degrees, or the like. In one or more embodiments, the first needle 604 may be used to reach the sub-ligamentous space. In one or more embodiments, the second needle 606 may be configured to curve with the curvature of the insertion end 612. That is, the second needle 606 may curve with the concave shape of the insertion end 612, such that the path of the second needle 606 may follow a portion of the path of the concaved shaped end of the first needle 604.

In one or more cases, to begin the ALL approach as illustrated in FIGS. 6A-6B, the user may administer light anesthesia to the injection site. The light anesthesia may allow a patient to provide feedback to the user to facilitate safe passage of the first needle 604 of the tool 600 underneath the lateral margin of the anterior longitudinal ligament 302 and into the sub-ligamentous space 312. For example, the patient may inform the user if the patient is feeling paresthesia or discomfort, which would indicate to the user that the tool 600 may have contacted a portion of the spinal root nerve 216.

In one or more embodiments, to enter an anterolateral portion or an anterior portion of the intervertebral disc 206 via the ALL approach, a user inserts the tool 600, being configured in a default position 614, into a portion of the patient's back at or near the target disc. Using image-guidance, such as viewing an x-ray of the injection site and area surrounding the target disc, the user may guide the tool 600, in particular the insertion end 612 of the first needle 604, from a posterolateral side of the intervertebral disc 206 to the sub-ligamentous space 312. The insertion end 612 of the first needle 604 may be configured to facilitate insertion between anterior longitudinal ligament 302 and the annulus 306 of the intervertebral disc 206. The insertion end 612 of the first needle 604 may be inserted between the two types of tissue, and through a rocking motion, can split the two tissues apart and be advanced into the sub-ligamentous space 312. The insertion end 612 may be parallel to the interface of the anterior longitudinal ligament 302 and the outer surface of the intervertebral disc 206. The user may guide the insertion end 612 of the first needle 604 in the sub-ligamentous space 312 (i.e., beneath the anterior longitudinal ligament 302) up to one half the width of the anterior longitudinal ligament 302 while remaining in the sub-ligamentous space 312. In one or more embodiments, the user may guide the insertion end 612 of the first needle 604 in the sub-ligamentous space 312, preferably without creating needle tracks in the posterior longitudinal ligament 304. In one or more embodiments, the user may guide the insertion end 612 of the first needle 604 in the sub-ligamentous space 312 without moving the lateral margin of the anterior longitudinal ligament 302 or by moving the lateral margin of the anterior longitudinal ligament 302 with a retractor.

Similar to positioning the insertion angle of the second needle 606 in the posterior transforaminal approach using tool 100, the user may optionally rotate the tool 600 to position the insertion angle of the second needle 606 into the intervertebral disc 206. In one or more cases, the user may rotate the tool 600 within the sub-ligamentous space 312 to position the insertion angle of the second needle 606. The user may use the switch 608 as a guide to align the insertion angle of the second needle 606.

Having positioned the insertion angle of the second needle 606, the user may configure the tool 600 into a deployed position 616. To configure the tool 600 into the deployed position 616, the user may move the switch 608 along the outer surface of the handle 602, thereby deploying the second needle 606 out of the first needle 604. The deployed second needle 606 may breach at least a portion of the annulus 306. In one or more embodiments, the insertion end 621 of the second needle 606 is configured to enter at least a portion of the nucleus 308 for the cases in which the switch 608 is moved to a full deployed length (e.g., the switch 608 being moved a distance of 100 percent of the track within the handle 602) or near fully deployed length (e.g., the switch 608 being moved a distance of 65 percent to 99 percent of the track within the handle 602) of the second needle 606. Having entered at least a portion of the nucleus 308, the user may administer the therapeutic material to the nucleus 308. In one or more embodiments, the insertion end 621 of the second needle 606 is configured to be positioned within a portion of the annulus 306 for the cases in which the switch 608 is moved partially into the deployed position 616 (e.g., the switch 608 being moved a distance of 10 percent to 64 percent of the track within the handle 602), thereby allowing the user to administer the therapeutic material intra-annularly. Once the insertion end 621 of the second needle 606 is positioned within the intervertebral disc 206, the therapeutic material is delivered to the intervertebral disc 206 via the second needle 606.

Subsequent to completing the delivery of the therapeutic material, the user may move the switch 608 into the default position 614 to retract the second needle 606 into the first needle 604. When the tool 600 is configured in the default position 614, the first needle 604 can be withdrawn from the patient. The user may withdraw the first needle 604 along the same path in which the first needle 606 entered the sub-ligamentous space 312. In one or more embodiments, by removing the first needle 604 from the sub-ligamentous space 312, the anterior longitudinal ligament 302 may seal or partially seal the needle track, thereby acting as an endogenous bandage to allow for healing of the needle track and to ensure that all or substantially all of the dose of the therapeutic material is retained within the intervertebral disc 206. For the cases in which the second needle 606 fully penetrated the annulus 306 and entered the nucleus 308, the stiff collagenous structures of the anterior longitudinal ligament 302 may act to block the full-thickness transannular needle track created by the second needle 606.

What is claimed is:

1. A method of delivering therapeutic materials to an intervertebral disc via a sub-ligamentous space, the method comprising:
    positioning a tool at an interface of a longitudinal ligament and an outer surface of the intervertebral disc, the interface being the sub-ligamentous space, the tool comprising a first needle and a second needle housed within the first needle, and an insertion end of the first needle comprising a beveled end;
    inserting the insertion end of the first needle into the sub-ligamentous space;
    deploying the second needle from within the first needle into at least one of an annulus and a nucleus of the intervertebral disc; and
    delivering the therapeutic materials to the at least one of the annulus and the nucleus.

2. The method of claim 1, wherein positioning the tool at the interface comprises guiding the tool through a region of a foramen, the region being beneath a spinal nerve root and anterior to a spinal cord, to the intervertebral disc;
    wherein the longitudinal ligament comprises a posterior longitudinal ligament; and wherein inserting the first needle into the sub-ligamentous space comprises inserting the insertion end of the first needle beneath the posterior longitudinal ligament.

3. The method of claim 2, wherein inserting the first needle into the sub-ligamentous space comprises inserting the insertion end of the first needle up to one half the width of the posterior longitudinal ligament.

4. The method of claim 1, further comprising positioning the second needle into the intervertebral disc by positioning an indicator coupled with the tool 180° from an angle of curvature of the second needle.

5. The method of claim 1, further comprising positioning an opening of the insertion end of the first needle in a direction towards the annulus.

6. The method of claim 1, wherein the first needle is an elongated rigid tube, and wherein the insertion end is formed at an angle ranging from 20 to 30 degrees.

7. The method of claim 1, wherein the second needle is an elongated flexible tube having a tactile-tip end, and wherein the second needle is formed out of a shape memory alloy.

8. The method of claim 1, wherein the tool comprises a spring system configured to move the tool from a retracted position to a deployed position,
wherein the spring system comprises at least a plate and a switch coupled to one another, the plate being positioned within the tool and coupled to the second needle, the switch being configured to move along an outer surface of the tool, and
wherein the plate is configured to deploy and retract the second needle from the first needle based on a direction of movement of the switch.

9. The method of claim 1, wherein the longitudinal ligament comprises an anterior longitudinal ligament; and
wherein inserting the first needle into the sub-ligamentous space comprises inserting the insertion end of the first needle beneath the anterior longitudinal ligament.

10. The method of claim 1, wherein positioning the tool at the interface of the longitudinal ligament and an outer surface of the intervertebral disc comprises positioning the tool parallel to the interface of the longitudinal ligament and an outer surface of the intervertebral disc.

11. The method of claim 1, wherein positioning the tool at the interface comprises guiding the tool through a Kambin's Triangle located adjacent to the intervertebral disc;
wherein the longitudinal ligament comprises a posterior longitudinal ligament; and
wherein inserting the first needle into the sub-ligamentous space comprises inserting the insertion end of the first needle beneath the posterior longitudinal ligament.

12. The method of claim 1, wherein deploying the second needle from within the first needle into at least one of the annulus and the nucleus of the intervertebral disc comprises deploying the second needle into at least one of the annulus and the nucleus of the intervertebral disc via a posterior portion or a posterolateral portion of the intervertebral disc.

13. The method of claim 1, wherein deploying the second needle from within the first needle into at least one of the annulus and the nucleus of the intervertebral disc comprises deploying the second needle into at least one of the annulus and the nucleus of the intervertebral disc via an anterior portion or an anterolateral portion of the intervertebral disc.

14. A posterolateral transforaminal method of delivering therapeutic materials to an intervertebral disc, the method comprising:
positioning a tool at an interface of a posterior longitudinal ligament and an outer surface of the intervertebral disc, the interface being sub-ligamentous space, the tool comprising a first needle and a second needle housed within the first needle, and an insertion end of the first needle comprising a beveled end;
inserting the insertion end of the first needle into the sub-ligamentous space;
deploying the second needle from within the first needle into at least one of an annulus and a nucleus of the intervertebral disc, via a posterior portion or a posterolateral portion of the intervertebral disc; and
delivering the therapeutic materials to the at least one of the annulus and the nucleus.

15. The posterolateral transforaminal method of claim 14, wherein inserting the first needle into the sub-ligamentous space comprises inserting the insertion end of the first needle up to one half the width of the posterior longitudinal ligament.

16. The posterolateral transforaminal method of claim 14, wherein the first needle is an elongated rigid tube, and wherein the insertion end is formed at an angle ranging from 20 to 30 degrees.

17. The posterolateral transforaminal method of claim 14, wherein positioning the tool at the interface of the longitudinal ligament and an outer surface of the intervertebral disc comprises positioning the tool parallel to the interface of the longitudinal ligament and an outer surface of the intervertebral disc.

18. A method of delivering therapeutic materials to an intervertebral disc, the method comprising:
positioning a tool at an interface of an anterior longitudinal ligament and an outer surface of the intervertebral disc, the interface being sub-ligamentous space, the tool comprising a first needle and a second neede housed within the first needle, and an insertion end of the first needle comprising a beveled end;
inserting the insertion end of the first needle into the sub-ligamentous space;
deploying the second needle from within the first needle into at least one of an annulus and a nucleus of the intervertebral disc, via an anterior portion or an anterolateral portion of the intervertebral disc; and
delivering the therapeutic materials to the at least one of the annulus and the nucleus.

19. The method of claim 18, wherein inserting the insertion end of the first needle into the sub-ligamentous space comprises inserting the insertion end of the first needle from a posterolateral side of the intervertebral disc.

20. The method of claim 18, wherein the insertion end of the first needle comprises a curved shape, and
wherein inserting the insertion end of the first needle into the sub-ligamentous space comprises inserting the insertion end of the first needle from an anterolateral side of the intervertebral disc.

* * * * *